United States Patent [19]

Monte et al.

[11] 3,953,294

[45] Apr. 27, 1976

[54] TRANSAMINASE ASSAY

[75] Inventors: Alexander A. Monte; Ching Chiang, both of Glendora, Calif.

[73] Assignee: Mallinckrodt, Inc., St. Louis, Mo.

[22] Filed: May 6, 1974

[21] Appl. No.: 467,320

Related U.S. Application Data

[60] Division of Ser. No. 200,552, Nov. 19, 1971, Pat. No. 3,816,262, which is a continuation-in-part of Ser. No. 190,883, Oct. 20, 1971, abandoned.

[52] U.S. Cl. .................... 195/103.5 R; 23/230 B; 195/63; 195/68; 195/99
[51] Int. Cl.² .................. G01N 31/14; C07G 7/02
[58] Field of Search ................ 195/63, 68, 103.5 R, 195/100, 99; 23/230 B

[56] References Cited
UNITED STATES PATENTS

| | | | |
|---|---|---|---|
| 3,527,332 | 9/1970 | Deutsch | 195/63 X |
| 3,546,074 | 12/1970 | Deutsch | 195/63 X |
| 3,627,688 | 12/1971 | McCarty et al. | 195/63 X |
| 3,764,478 | 10/1973 | Bergmeyer et al. | 195/103.5 R |
| 3,858,854 | 1/1975 | Win et al. | 195/63 X |

*Primary Examiner*—David M. Naff
*Attorney, Agent, or Firm*—Mathew D. Madsen

[57] ABSTRACT

Glutamic oxaloacetic transaminase and glutamic pyruvic transaminase are determined using granular water-soluble substantially anhydrous, storage stable reagent formulations comprising a nitrogen-containing polyoxyalkylene nonionic surfactant obtained by the sequential reaction of ethylene diamine with propylene oxide and ethylene oxide in the presence of a catalyst. The surfactant contains, polyoxypropylene chains having an average molecular weight of between about 750 and about 6,750 and polyoxyethylene chains constituting between about 10 and about 80 weight percent of the surfactant. The surfactant has an advantageous effect upon granulation, dissolution and storage stability of the anhydrous reagent formulations, and is effective for solubilizing proteins.

24 Claims, 1 Drawing Figure

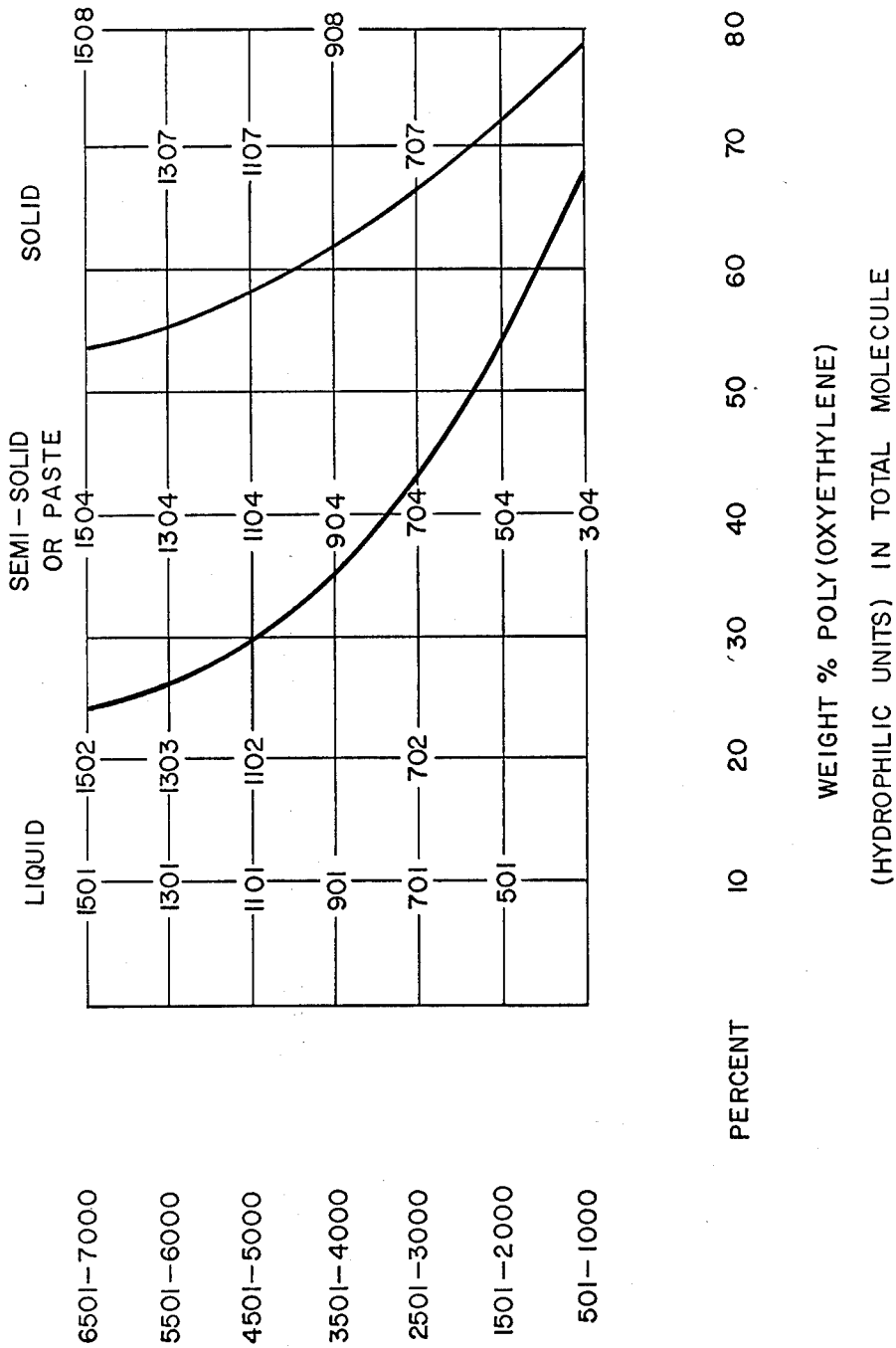

TRANSAMINASE ASSAY

This application is a division of our copending, coassigned U.S. Pat. application Ser. No. 200,552, filed Nov. 19, 1971, now U.S. Pat. No. 3,816,262, which is a continuation-in-part of our U.S. Pat. application Ser. No. 190,883, filed Oct. 20, 1971, now abandoned.

BACKGROUND OF THE INVENTION

This invention relates to the field of clinical diagnostic testing and more particularly to novel reagents and methods for making biological assays on body fluids.

A large variety of test reagents and methods are available for use in determining the character of various body fluids to assist in the diagnosis of certain pathological conditions. Tests for determination of certain types of biological activity or the presence and quantity of certain biologically active components provide information indicating the presence or absence of disease or other physiological disorder. In accordance with such tests, the biological specimen to be analyzed, for example, a sample of a body fluid, is typically mixed with a liquid reagent formulation which contains a reagent capable of effecting a reaction which causes a measurable change in the specimen/reagent system. Very often the reaction which takes place in the test is an enzymatic reaction. Certain tests are designed, in fact, to determine the presence of a particular enzyme and in such cases the reagent formulation may contain a substrate upon which the enzyme to be determined is known to act. In other cases, the determination may be for a material which is known to be a reactive substrate in an enzymatically catalyzed reaction. In either case, the reagent formulation very commonly contains an enzyme, a coenzyme or both. Because the catalytic activity of most enzymes is specific to a particular reaction, test reagents can be formulated which are effective to determine specific biological components or activities even in a complex body fluid containing a large number of other components which might interfere with efforts to obtain a purely chemical analysis. Moreover, many of the components which are to be determined have highly complex chemical structures which would render direct chemical analysis difficult even in the absence of any contaminants.

Unfortunately, enzymes and coenzymes are generally rather delicate materials which may be readily denatured by heating and which also tend to degenerate upon storage. Many of the substrate materials used in biological assay reagent formulations are similarly unstable. Liquid reagents containing such components are therefore not generally susceptible to storage and must be freshly prepared shortly prior to use in clinical diagnostic testing. Because of the relative expense of enzymes and coenzymes and the skill required to prepare a reagent formulation containing these materials which can be utilized to obtain accurate clinical diagnostic test results, the instability of the liquid formulations has motivated a substantial amount of research to develop reagents in a relatively storage-stable form. Much of this effort has been directed to the development of solid, dry, water-soluble formulations which can be dissolved in water at the time of testing to provide a fresh liquid reagent useful in the test. Typical prior art dry reagent formulations are disclosed in Deutsch U.S. Pat. No. 3,413,198 and Stern et al. U.S. Pat. No. 3,546,131.

A dry reagent formulation satisfactory for use in preparing liquid reagents for routine clinical diagnostic tests should satisfy a number of criteria. It must be readily soluble in a solvent compatible with the biological specimen, usually water. It should be capable of solubilizing proteinaceous material in the specimen. Moreover, it should be readily susceptible to packaging in convenient sized packages and be adapted for rapid dissolution in the solvent to provide a liquid reagent of proper strength for a given test or series of tests.

SUMMARY OF THE INVENTION

It is an object of the present invention to provide improved dry, water-soluble, reagent formulations for use in conducting clinical diagnostic tests. It is a further object of the present invention to provide such formulations which can be readily granulated and shipped or stored in granular form. It is a particular object of the invention to provide such reagent formulations in free-flowing, granular form at consistent bulk densities so that they may be delivered to a volumetric packaging or tableting operation in consistent weight amounts. Additional objects of the invention include the provision of dry reagent formulations having a high capacity for solubilizing protein; the provision of such formulations having a high degree of storage stability; the provision of methods for preparing the dry reagent formulations of the invention; and the provision of methods for conducting clinical diagnostic tests utilizing such reagent formulations. Other objects and features will be in part apparent and in part pointed out hereinafter.

In one of its aspects, therefore, the present invention is directed to a reagent formulation for use in conducting a clinical diagnostic test on a biological specimen. The reagent formulation comprises a solid, water-soluble, substantially anhydrous, storage-stable mixture containing a reagent capable of participating in a test reaction to effect a measurable change in a test system, and a solid nitrogen-containing polyoxyalkylene nonionic surfactant. The surfactant has a structure corresponding to that obtained when ethylene diamine is reacted sequentially with propylene oxide and ethylene oxide in the presence of a catalyst and the polyoxypropylene chains of the surfactant have an average molecular weight of between about 750 and about 6750.

The invention is further directed to a method of conducting a clinical diagnostic test on a biological specimen using the aforementioned reagent formulation. The method comprises dissolving the reagent formulation in water to produce a liquid reagent; mixing the liquid reagent with a specimen to form a specimen/reagent test system; and measuring a change in the system resulting from the reaction between the reagent and the specimen.

The invention is also directed to a method of preparing the novel reagent formulation. The method comprises the steps of mixing a reagent capable of participating in a test reaction to effect a measurable change in a test system, a nitrogen-containing polyoxyalkylene nonionic surfactant of the above-noted character, and a solvent for the surfactant; and removing the solvent to form a substantially anhydrous, water-soluble, free-flowing, granular solid.

DESCRIPTION OF THE DRAWING

The DRAWING is a grid illustrating the molecular structure of various commercially available nonionic surfactants useful in the practice of the invention. The coordinates of each point on the grid correspond to the chain size of the polyoxyethylene hydrophile and polyoxypropylene hydrophobe moieties of a particular surfactant. Boundary lines set out on the grid separate the areas encompassing surfactants which assume different physical states.

DESCRIPTION OF THE PREFERRED EMBODIMENTS

To facilitate preparation of liquid reagents from solid formulations in the clinical laboratory, it is highly desirable to package the solid formulations in proper unitary amounts. Thus, for example, the solid formulations may be encapsulated or tabletted with the proper quantity of reagent in each capsule or tablet for conducting a single test. Alternatively, a multi-test package can be provided from which the proper amount of liquid reagent is prepared for conducting a specified number of tests.

Where a solid reagent formulation is packaged in unitary amounts, accuracy of metering the solid material into each capsule, tablet or multi-test package is important. The metering equipment which is used for delivering solid materials in packaging and tableting operations, however, almost universally operates on a volumetric basis. Unless the solid material is free-flowing and has a consistent bulk density, therefore, it cannot be delivered in consistent weight amounts to each package, capsule or tableting station using conventional equipment.

To provide a solid formulation in free-flowing form of consistent bulk density, it is preferably granulated prior to packaging. Granulation converts a powdered material into a material constituted by small agglomerates of relatively uniform size. Properly prepared, the granular material is free-flowing, has a consistent bulk density and is readily handled by the metering devices used in packaging operations. To granulate a powdered material, the powder is typically mixed with a binder dissolved in a volatile solvent, wet screened, dried by driving off the solvent, and dry screened following the drying step. In addition to the binder, a lubricating substance is normally incorporated in the granulation mass to further enhance the flow characteristics of the granules, especially under the compressive stress of tableting operations.

As noted, solid formulations useful as reagents for conducting clinical diagnostic tests on biological specimens should have certain additional properties. Because they are dissolved in water to produce a liquid reagent, all components, including the binder, should be readily water-soluble. Because many of the tests involve enzymatic reactions and/or proteinaceous substrates, the formulation should possess detergent properties for solubilizing protein.

It has now been discovered that the above objectives can be met and that effective clinical reagent formulations for the determination of certain biological properties of body fluids can be produced in free-flowing, granular form through the use of particular nitrogen-bearing polyoxyalkylene nonionic surfactants. Test formulations granulated with the aid of these surfactants are well adapted to precision packaging and tableting operations. Because of their free-flowing character and consistent bulk density, they can be delivered to either a packaging or tableting operation in consistent weight amounts by volumetric metering. As a consequence, clinical test reagents formulated at a central location remote from a clinical laboratory can be utilized to prepare liquid test reagents for clinical use without the need for weighing, analyzing, or other procedures by the clinical chemist or technician.

The nitrogen-containing surfactants which are useful in the formulations of the invention possess the unique multiple capability of serving as binders, lubricants and solubilizers for protein. Moreover, they are themselves water-soluble, thus promoting the dissolution of the reagent formulations in water to provide clinical liquid reagents. These surfactants are sold under the trade designation "Tetronic" by Wyandotte Chemical Corporation. They are normally prepared by sequential reaction of first propylene oxide and then ethylene oxide with ethylene diamine in the presence of an alkaline or acid catalyst. Normally these surfactants are prepared at elevated temperatures using alkaline catalysts such as sodium hydroxide, potassium hydroxide, sodium alkoxide, quarternary ammonium bases and the like. Other methods are available for the preparation of these surfactants. The preparation of surfactants such as those utilized in the formulations of the invention is more fully described in U.S. Pat. No. 2,979,528.

The properties and physical state of nonionic surfactants having structures corresponding to those derived from ethylene diamine, propylene oxide and ethylene oxide vary with the lengths of the polyoxypropylene and polyoxyethylene chains. As the drawing shows, the physical state of these surfactants is largely dependent upon the proportionate weight of the surfactant constituted by the polyoxyethylene chains, but is also influenced by the average molecular weight of the polyoxypropylene moieties. The polyoxypropylene chains are hydrophobic while the polyoxyethylene chains are hydrophilic. Thus, the surfactants having polyoxypropylene units of low average molecular weight are more water-soluble than those having polyoxypropylene units of a higher average molecular weight. The numbers set out on the face of the grid correspond to particular members of the Tetronic series. Each number is located at a point on the grid whose coordinates correspond to the polyoxyethylene and polyoxypropylene chain sizes of the particular product which is commercially designated by said number.

Essentially any surfactant whose structure is defined by the coordinants of a point lying in the grid of the drawing may be utilized in the formulations of the invention. It is preferred, however, that the surfacant be solid or at least semi-solid. A greater proportion of the solid surfactants can be satisfactorily incorporated in a reagent formulation and thus a greater binding and lubricating capacity is obtained without adversely affecting other properties of the formulation. Desirably, on the order of 2.5 to 5% by weight of the preferred solid surfactants are incorporated in the reagent formulations. When the liquid formulations are used, it is not always possible to incorporate more than 2 or 3% by weight of the surfactant without imparting a somewhat waxy character to the formulation. The use of 2 to 3% by weight of a liquid Tetronic surfactant produces a useful product, but the binding and lubricating capabilities of the surfactant are not always fully exploited at such a level. Granules having the most desirable properties are obtained using solid or semi-solid surfactants.

Since the dry reagent formulations of the invention are dissolved in water for use in conducting clinical diagnostic tests, it is also desirable that the surfactant component promote the dissolution of the granular product. Thus, it is preferred that the surfactant be as hydrophilic as possible, i.e., that the molecular weight of the polyoxypropylene hydrophobe moiety of the surfactant be relatively low. Thus, the preferred surfactants for use in the formulations of the invention are those which are both solid or semi-solid in physical state and relatively hydrophilic. Solid-state surfactants with polyoxypropylene chains having an average molecular weight of less than about 4000 are especially preferred, with the most suitable surfactants being those whose polyoxypropylene chains have an average molecular weight of between about 2,750 and about 3,750 and whose weight percentage of polyoxyethylene units is between about 70 and about 80%. Two particular surfactants whose weight and structure characteristics fall within the latter limits are those sold under the trade designations Tetronic 707 and Tetronic 908. Tetronic 707 has a polyoxypropylene hydrophobe molecular weight on the order of 2,750 and a weight percentage of polyoxyethylene units of about 70% while Tetronic 908 has a polyoxypropylene molecular weight of about 3750 and a weight percentage of polyoxyethylene units of about 80%. Good results are also obtained with surfactants whose polyoxypropylene chains have an average molecular weight of between 750 and 4,000 with a weight percentage of between about 35% and about 65% polyoxyethylene units. Other surfactants within the grid of the drawing are reasonably satisfactory but less effective than those represented by the right lower corner of the grid.

In addition to their advantageous effect upon granulation and dissolution of dry clinical test reagent formulations, surfactants of the above-noted character have been found to be effective for solubilizing protein. As indicated above, this is a highly advantageous characteristic, since enzymes and other proteinaceous matter derived from either the reagent formulation or the specimen commonly participate in the test reactions. By solubilizing protein, the surfactants function to facilitate the progress of the test reaction and thus enhance the effectiveness of the reagent formulation. It may, therefore, be seen that incorporation of these surfactants in clinical test formulations uniquely provides multiple advantages in the preparation, packaging, dissolution and functional operation of clinical reagent formulations.

It has further been discovered that the dry clinical reagent formulations of the invention are quite stable and generally possess good shelf life characteristics. Although we cannot precisely account for the particular ingredient or combination of ingredients which imparts the high degree of storage stability, it appears that such stability may be a somewhat general characteristic of dry clinical reagent formulations which include the particular nitrogen-containing nonionic surfactants used in our formulations. If so, the ability to impart storage-stability represents a further aspect of the unique multiple function of this type of surfactant in such formulations.

To prepare the reagent formulations of the invention, the surfactant is mixed with a volatile solvent and at least one reagent capable of participating in a test reaction to effect a measurable change in a reagent/specimen test system. The surfactant should be soluble up to the amount present in the solvent which is utilized. Solvents which may be used include methylene chloride, chloroform, methanol, benzene, water, methanol/water, and chloroform/methylene chloride. After thorough mixing and appropriate size classification, the solvent is removed to yield a granular product.

In a preferred embodiment of the invention, the ingredients of the formulation, in dry particulate form, are thoroughly blended in a mechanical mixer. With the mixer running, a granulating solution containing the solvent and the surfactant, preferably that sold under the trade designation Tetronic 707 or Tetronic 908, is added. Additional solvent is used as needed to produce granular agglomerates of the desired size and wetness.

The resulting wet granulation is screened through a coarse screen, for example 10 mesh, then spread in thin layers in trays and dried at reduced pressure, for example, 25 inches Hg absolute or less. Depending on the heat sensitivity of the formulation, drying is normally carried out at room temperature or at modest elevated temperature (up to about 37°C.). Generally, the depth of the wet granules in the trays should not exceed about one-half inch to three-fourths inch.

After completion of the drying cycle, the dried granulation is rescreened through a finer screen, for example, 20 to 30 mesh, blended thoroughly and packaged in containers essentially impervious to moisture. Since the components of the reagent formulation are frequently moisture sensitive, the formulation should not be exposed to a relative humidity of more than about 5% after removal from the dryer.

The reagent formulations of the invention are adapted to be packaged in small unitary packages. For example, sufficient reagent formulation for a single assay may be tabletted or packaged in a capsule. The reagent formulations are also adapted to packaging in such containers as foil strip packets, utilizing automatic packaging machinery. Utilizing this packaging approach, sufficient reagent formulation to carry out a suitable predetermined number of tests, such as 10, 25, or 50 tests, may be accurately packaged in a single foil packet. The user then simply dissolves the contents of the multiple test packet in a predetermined volume of water and uses a suitable aliquot of the resulting liquid reagent in the performance of each of a series of assays for the desired biological substance or property.

In some instances, depending on the nature of the components and their compatibility, all of the reagents necessary in a single assay or determination may be included in a single formulation. In other instances, incompatabilities and/or other considerations may make it desirable to segregate certain reagents in which case two or more reagent formulations are prepared in accordance with the invention.

To conduct a clinical diagnostic test using the formulations of the invention, the liquid reagent produced by dissolving the dry formulation in a predetermined amount of water is mixed with the biological specimen in a predetermined volumetric or weight ratio. With the aid of appropriate instrumentation as required, the resulting specimen/reagent system is observed for the presence, absence, nature and extent of a physical, chemical or biological change. Such change as does occur is measured to provide the desired information for use in the clinical diagnosis.

Exemplary reagent formulations prepared in accordance with the invention and useful for the determination of hemoglobin, blood urea nitrogen, total protein, serum glutamic oxaloacetic transaminase, alkaline phosphatase, glucose, inorganic phosphorus, lactate dehydrogenase-L, serum glutamic pyruvic transaminase, uric acid (colorimetric) and uric acid (u.v.) are set forth in Table 1. The preferred compositions of these reagent formulations and methods for preparing them are described in the examples following Table 1 which more fully illustrate the invention.

5 minutes, then packaged in tightly closed containers. Approximately 1000 g. of a water-soluble, substantially anhydrous reagent formulation, sufficient for 50,000 tests, was obtained.

Upon being stored at a temperature of 45°C., the

Table 1

Exemplary Clinical Test Reagent Formulations

| Formulation | Type of Formulation | Dry Ingredients (Reagents, Etc.) Name/Formula | Wt. (g.) | TETRONIC 707 (g.) | Polyethylene glycol 6000 (g.) | $CH_2Cl_2$ (ml.) (1) | Theoretical Yield (g.) | No. of Tests (Thousands) |
|---|---|---|---|---|---|---|---|---|
| A | Reagent Formulation for Hemoglobin Assay | $NaHCO_3$<br>$K_3Fe(CN)_6$<br>KCN<br>Mannitol | 300<br>50<br>30<br>590 | 30 | | (a) 200<br>(b) 300 | 1000 | 50 |
| F | Coenzyme Formulation for GOT Assay | L.-Aspartic Acid<br>MDH Formulation (containing 6.0 mg. MDH; 1.4 I.U.)<br>NADH Formulation (containing 0.5 mg. NADH)<br>Tris-(hydroxymethyl)-aminomethane<br>Succinic Acid | 1250<br><br><br><br><br><br>1875<br>187.5 | 80 | | (a) 800<br>(b) 525 | | 25 |
| G | Substrate Formulation for GOT Assay | Sodium Alpha-Ketoglutarate<br>Mannitol | 200<br>765 | 25 | | (a) 500<br>(b) 200 | 990 | 50 |
| R | Coenzyme Formulation for Serum Glutamic Pyruvic Transaminase Assay | NADH Formulation (equivalent to 0.4 mg. NADH)<br>LDH Formulation (equivalent to 2 units LDH)<br>DL-Alanine<br>Sodium phosphate, dibasic<br>Sodium phosphate, monobasic | <br><br><br><br>1200<br>585<br>75 | 50.4 | | (a) 200<br>(b) 70 | | 15 |
| S | Substrate Formulation for Serum Glutamic Pyruvic Transaminase Assay | (See formulation G Above) | | | | | | |

(1) (a) indicates amount of $CH_2Cl_2$ used as carrier for Tetronic 707
 (b) indicates amount of additional $CH_2Cl_2$ used to optimize granulation

EXAMPLE 1

Hemoglobin Reagent Formulation and Assay

Composition of the reagent formulation useful for hemoglobin assay is set forth as formulation A in Table 1.

To prepare this formulation, sodium bicarbonate (300 g.), milled potassium ferricyanide (50 g.) and potassium cyanide (30 g.) were initially added to a Hobart bowl and mixed with a stainless steel spatula. Mannitol (590 g.) was then added and the resulting blend was agitated for five minutes in the mixer. While agitation was continued, a solution of Tetronic 707 (30 g.) in methylene chloride (200 ml.) was added. An additional amount of methylene chloride (300 ml.) was then added to produce the proper granulation.

The wet granulation was screened through a No. 10 mesh stainless steel screen and the wet screened material was transferred to 8 × 12 inches Pyrex drying trays, at a depth of between about one-half inch and about three-fourths inches in each tray. The granulation was then dried in a vacuum oven for 15 hours at a temperature of 35°C. and a pressure of 25 inches Hg.

The dried granulation was removed from the vacuum oven in an environment where the relative humidity was not more than 5%. The dried granulation was then screened through a No. 20 mesh stainless steel screen using an Erweka oscillator. The screened, dried granulation was transferred to a P.K. blender and mixed for above-prepared formulation was found to be stable for at least 23 weeks which is equivalent to a stability period of 92 weeks at room temperature.

Dissolved in water, formulation A yields a liquid reagent useful in assaying blood hemoglobin. By action of the dissolved reagent, erythrocytes in the blood are hemolyzed releasing hemoglobin which is oxidized to methemoglobin. Methemoglobin is converted to cyanmethemoglobin whose formation alters the optical density of the reagent/specimen system. The optical density of the reagent/specimen system is measured at 540 nm. using a suitable spectrophotometer and compared against a reagent blank set at 100% transmission. The hemoglobin level is then determined by reference to a standard curve.

To prepare a liquid reagent sufficient for 50 tests, formulation A (1.00 g.) is dissolved in distilled water and the resulting solution is diluted to 250 ml. and mixed thoroughly. The reagent solution thus produced is stable for three months at room temperature if protected from light.

To conduct the hemoglobin assay test, a reagent/-specimen test system is prepared by adding 20 microliters of well mixed blood (collected with an anticoagulant) to 5 ml. of the above solution of formulation A in a clean test tube. The contents of the tube are mixed thoroughly and allowed to stand at room temperature for at least five minutes. The optical density is then measured as described above to determine the hemoglobin level.

EXAMPLE 2

Serum Glutamic Oxaloacetic Transaminase Formulations and Assay

For the serum glutamic oxaloacetic transaminase (SGOT) test, two separate formulations are provided. The two formulations which are utilized are set forth in Table 1 as formulations F and G. Predetermined amounts of these formulations are dissolved in separate portions of water to provide liquid reagents for use in making the SGOT assay.

Preparatory to blending the constituents of coenzyme formulation F, the modified malate dehydrogenase and reduced nicotinamide adenine dinucleotide components are prepared.

Modified malate dehydrogenase was derived from yellow split peas. The peas were pulverized to a fine powder using a mill or a micromill. A saturated solution of potassium chloride was prepared at room temperature by stirring potassium chloride (500 g.) in approximately 1 l. of distilled water for 5 minutes and allowing the solution to stand at room temperature overnight. Pulverized pea powder (10 g.) was stirred into a 50 ml. portion of the saturated potassium chloride solution, which extracted the malate dehydrogenase therefrom. Extraction was carried out at room temperature for approximately 3 hours with occasional stirring. At the end of the 3 hour extraction period, the resulting suspension was centrifuged at 10,000 rpm using a No. 872 angle rotor in an IEC B-20 refrigerated centrifuge at 10°C. for 10 minutes. The slightly colloidal supernatant extract fluid was collected and transferred to a plurality of freeze drying vessels. The extract was frozen in thin layers by rotating each vessel in a dry ice/alcohol bath at −60°C. or below. The frozen thin layers were lyophilized at −60°C. to −70°C. and an absolute pressure of 5 m$\mu$ Hg for 18 to 20 hours. The resultant lyophilized powder was collected under an atmosphere having a relative humidity of less than 5% and stored in a dessicator at 4°C. Approximately 14 g. of dry powder was obtained which was assayed for the enzymic activities of both malate dehydrogenase (MDH) and glutamic oxaloacetic transaminase (GOT). GOT specific activities was less than about 0.05% in relation to MDH specific activity, and the extract enzyme was, therefore, suitable for use. Activity of the MDH obtained was 1.4 I.U./6 mg.

To prepare modified reduced nicotinamide adenine dinucleotide (NADH), gum arabic (15 g.), tris-(hdroxymethyl)-aminomethane (12 g.), "Amisol" (10 g.), and bovine serum albumin (0.5 g.) were dissolved in distilled water (450 ml.) and the resulting solution was titrated to pH 9.0 with 12N sulfuric acid. After titration, the solution was diluted to 500 milliliters with distilled water and clarified by centrifugation at 10,000 rpm with a No. 872 angle rotor in an IEC B-20 refrigerated centrifuge at 10°C. for 16 minutes. To the supernatant obtained from this centrifugation, 10 g. of NADH powder (reduced nicotinamide adenine dinucleotide disodium salt) was added and the resulting mixture stirred for at least 5 minutes to insure good mixing. This mixture was transferred into freeze drying vessels and frozen in thin layers by rotating the vessels in a dry ice/alcohol bath at −60°C. or below. The frozen thin layers were lyophilized for 20 to 24 hours at −60°C. to −70°C. and an absolute pressure of 5 m$\mu$ Hg. The resultant lyophilized powder was collected under an atmosphere having a relative humidity of less than 5% and stored in a dessicator at 4°C. Approximately 50 g. of dry lyophilized powder was obtained.

To prepare coenzyme formulation F L-aspartic acid (1,250 g.), the above modified MDH (equivalent to 1.4 I.U. or 6.0 milligrams MDH), the above modified NADH (equivalent to 0.5 milligrams NADH), tris-(hydroxymethyl)-aminoethane (1,875 g.), and milled succinic acid (187.5 g.) were blended in a Hobart bowl mixer and agitated to promote intimate mixing. With the mixer running, a solution of Tetronic 707 (25 g.) in methylene chloride (800 ml.) was added to the blend. Additional methylene chloride (approximately 525 ml.) was subsequently introduced to produce the desired degree of granulation and wetness. The wet granulation was then screened and dried at room temperature, and the resulting dry granulation rescreened and packaged, in the manner described for hemoglobin reagent formulation A in Example 1.

To prepare substrate formulation G, sodium $\alpha$-ketoglutarate (200 g.) and lump-free mannitol (765 g.) were blended in a Hobart bowl and agitated to promote intimate mixing. With the mixer running, a solution of Tetronic 707 (25 g.) in methylene chloride (500 ml.) was added to the blend. Additional methylene chloride (approximately 200 ml.) was subsequently introduced to produce the desired degree of granulation and wetness. The Wet granulation was then screened and dried at room temperature and 25 inches pressure or less and the resulting dry granulation rescreened and packaged, in the manner described for hemoglobin reagent formulation A in Example 1.

Upon being stored at a temperature of 45°C., the above-prepared formulations were found to be stable for at least 3 weeks which is equivalent to a stability period of 12 weeks at room temperature.

Dissolved in separate portions of water, formulations F and G provide liquid reagents useful in assaying for serum glutamic oxaloacetic transaminase. SGOT present in the specimen catalyzes the transmination of L-aspartic acid and $\alpha$-ketoglutaric acid producing oxaloacetate and glutamate. The oxaloacetate and NADH in the presence of MDH are converted to malate and NAD. The extent of reaction is indicative of the SGOT present and is measured by observing a decrease in optical density at 340 nm. at 37°C.

The liquid reagent solution of formulation F is prepared by dissolving 7.2 g. of the formulation in distilled water, diluting to 125 ml. and mixing well. The solution of formulation G is prepared in similar fashion utilizing a 1.0 g. of the formulation and diluting to 25 ml. The formulation F solution should be prepared fresh daily while the formulation G solution is stable for a week under refrigeration.

In the conduct of the test, 2.5 ml. of the formulation F solution are placed in a test tube, 0.1 ml. of serum are added thereto, and the resulting solution stirred and incubated at 37°C. in a heating unit for 7 to 10 minutes. 0.5 ml. of the formulation G solution is then added and mixed quickly in less than 10 seconds at room temperature. Exactly 2 minutes after the liquid reagent solution of formulation G is added, the test tube is removed from the heating unit and the absorbance of the reagent/specimen system is measured. The tube is then returned to the heating unit and held there until exactly 5 minutes after the solution of formulation G was first added. At this point, the tube is again removed from the heating unit and the final absorbance of the reagent/specimen system is measured. The SGOT content is determined from the two absorbance readings by calculation utilizing the following equation:

$$\frac{A_1 - A_2}{L} \times 1667 = SGOT \text{ units/ml. serum}$$

where $A_1$ equals absorbance read at 2 minutes, $A_2$ equals absorbance read at 5 minutes, L equals light path of the absorption cell or the I.D. of the test tube in centimeters. An SGOT unit is defined as that amount of enzyme which catalyzes the oxidation of 0.001 micromole of NADH to NAD per minute, at 37°C. Other conditions for determining SGOT are known. The Karmen procedure known to the art carries out the above reactions at 25°C. instead of 37°C.

EXAMPLE 3

Serum Glutamic Pyruvic Transaminase Formulations and Assay

For the serum glutamic pyruvic transaminase test, two separate formulations are provided. The two formulations which are utilized are set forth in Table 1 as formulations R and S.

Preparatory to blending the constituents of coenzyme reagent formulation R, the modified lactate dehydrogenase and reduced nicotinamide adenine dinucleotide components are prepared. The modified NADH component was prepared in accordance with the method described in Example 4. Modified lactate dehydrogenase was prepared as described below.

Gum arabic (15 g.), ammonium sulfate (10 g.), tris-(hydroxymethyl)-aminomethane (12 g.), and bovine serum albumin (0.1 g.) were dissolved in distilled water (450 ml.). The resulting solution was titrated to a pH of 7.4 with 12N sulfuric acid and then diluted to a total volume of 500 ml. This solution was clarified by centrifugation at 10,000 rpm and a temperature of 10°C. for 16 minutes, using a No. 872 angle rotor in an IEC B-20 refrigerated centrifuge. To 300 ml. of the clarified solution was added an LDH crystalline suspension in ammonium sulfate solution (10 ml. containing 100 mg. LDH). The resulting enzyme mixture was stirred for 5 minutes to insure good mixing and then divided and each portion placed in one of several freeze-drying vessels. Each portion was then frozen in thin layers by rotating the vessel containing it in a dry ice/alcohol bath at −60°C. or below. The frozen thin layers were lyophilized at −60°C. to −70°C. at a total pressure of 5 m$\mu$ Hg for a period of 18–20 hours. The lyophilized powder obtained was collected under an atmosphere having a relative humidity of less than 5% and stored in a dessicator at 4°C. Approximately 26 g. of dry powder was obtained. This powder was assayed for the enzymatic activities of both glutamic pyruvic transaminase and LDH. The GPT specific activity was found to be less than 0.04% in relation to the LDH specific activity and the modified LDH lyophilized powder was therefore suitable for use in preparing formulation R.

In the preparation of enzyme reagent formulation R, modified NADH (having an equivalent NADH content of 0.4 mg.), modified LDH (having an LDH equivalent of 2 units), DL-alanine (1.20 kg.), dibasic sodium phosphate (585 g.), and milled monobasic sodium phosphate (750 g.) were blended in a Hobart bowl and agitated to promote intimate mixing. With the mixer running, a solution of Tetronic 707 (50.4 g.) in methylene dichloride (200 ml.) was added to the blend. Additional methylene chloride (approximately 70 ml.) was subsequently introduced to produce the desired degree of granulation. The wet granulation was then screened and dried at room temperature and the resultant dry granulation rescreened and packaged in the manner described in Example 1 for hemoglobin reagent formulation A.

Substrate reagent formulation S has essentially the same composition and was prepared in essentially the same manner as was formulation G of Example 4.

Dissolved in separate portions of water, formulations R and S provide liquid reagents useful in assaying for serum glutamic pyruvic transaminase (SGPT). SGPT present in the specimen catalyzes the transamination of L-alanine and $\alpha$-ketoglutaric acid producing a pyruvate and glutamate. Pyruvate and NADH, in the presence of LDH, are converted to lactate and NAD. The extent of reaction is indicative of the SGPT present and is measured by observing a change in optical density at 340 nm at 37°C.

To prepare a coenzyme liquid reagent solution, formulation R (6.55 g.) is dissolved in distilled water (125 ml.). A substrate liquid reagent is prepared by dissolving formulation S (1.00 g.) in distilled water (25 ml.). The resulting solutions are sufficient for 50 tests. The substrate liquid reagent is stable for 1 week when refrigerated. The coenzyme reagent formulation, on the other hand, should be prepared fresh daily.

In the conduct of the test, an aliquot of the solution of formulation R (2.5 ml.) is mixed with a serum specimen (100 $\mu$l) to form a reagent/specimen test system which is then preincubated at 37°C. for 7–10 minutes in a heating unit. After preincubation, an aliquot of the solution of reagent formulation S (0.5 ml.) C. is added to the test system and mixed in less than 10 seconds at room temperature. The container holding the system is returned to the heating unit where it is held at 37°C. Exactly 2 minutes after the solution of formulation S is added, the container is removed from the heating unit and the absorbance of the test system measured using a spectrophotometer which has previously been set at zero absorbance using distilled water as a blank. Immediately after the measurement is taken, the container is returned to the heating unit and held at 37°c. Exactly 5 minutes after the solution of formulation S is added (i.e., three minutes after the first reading), the container holding the test system is again removed from the heating unit and the absorbance again measured on the spectrophotometer. The SGPT content of the system is then determined in accordance with the following calculations:

$$\frac{A_1 - A_2}{L} \times 1665 = SGPT \text{ units per ml. serum}$$

where $A_1$ equals absorbance read at 2 minutes, $A_2$ equals absorbance read at 5 minutes and L equals the light path of the absorption cell or the I.D. of the container in centimeters.

An SGPT unit is defined as that amount of enzyme which catalyzes the oxidation of 0.001 micromoles per minute of NADH to NAD at 37°C. under the above test conditions. The Karmen procedure known to the art carries out the above reactions at 25°C. instead of 37°C. By definition, one Karmen unit is equal to 1.09 SGPT units, and SGPT units may therefore be converted to Karmen units by multiplying the SGPT units by 0.917.

If the absorbancy difference $(A_1 - A_2)$ observed in the above determination exceeds 0.225 a very high SGPT activity in the serum is indicated. At this level of activity, the relationship between the absorbency difference and the LDH units per milliliter of serum is not linear and the coefficient in the above-noted equation may be inaccurate, yielding inaccurate results. To provide greater accuracy in the measurement of high SGPT activities, the above-described test is repeated with a 20 μl serum sample and the activity calculated in accordance with the following equation:

$$\frac{A_1 - A_2}{L} \times 8100 = SGPT \text{ units per ml. serum}$$

It will be appreciated that the accuracy of the SGPT test is also highly dependent on close temperature control. Preferably, therefore, the cuvette compartment of the spectrophotometer used includes means for temperature control and the temperature of the specimen is controlled at 37°C. Where the instrument is not so-equipped with temperature control means, the absorption cell should not be removed from the heating unit for more than 10 seconds when making an optical density determination on the test system.

In view of the above, it will be seen that the several objects of the invention are achieved and other advantageous results attained.

As various changes could be made in the above methods and products without departing from the scope of the invention, it is intended that all matter contained in the above description shall be interpreted as illustrative and not in a limiting sense.

What is claimed is:

1. A reagent formulation for use in assaying a biological specimen for glutamic oxaloacetic transaminase comprising a granular, water-soluble, substantially anhydrous, storage-stable mixture containing L-aspartic acid, malate dehydrogenase, reduced nicotinamide adenine dinucleotide disodium salt, bovine serum albumin, a carbohydrate polymer, tris-(hydroxymethyl)-aminomethane, succinic acid, gum arabic, and a nitrogen-containing polyoxyalkylene nonionic surfactant obtained by the sequential reaction of ethylenediamine with propylene oxide and ethylene oxide in the presence of a catalyst, said surfactant containing polyoxypropylene chains having an average molecular weight of between about 750 and about 6,750 and polyoxyethylene chains constituting between about 10 and about 80 weight percent of said surfactant.

2. A reagent formulation as set forth in claim 1 wherein the nitrogen-containing surfactant is solid and the polyoxypropylene chains thereof have an average molecular weight of less than about 4,000.

3. A reagent formulation as set forth in claim 2 wherein the polyoxypropylene chains of the surfactant have an average molecular weight of about 2,750 and the weight percentage of the polyoxyethylene units thereof is about 70%.

4. A reagent formulation for use in assaying a biological specimen for a transaminase comprising a granular, water-soluble, substantially anhydrous, storage-stable mixture containing sodium alpha-ketoglutarate, mannitol, and a nitrogen-containing polyoxyalkylene nonionic surfactant obtained by the sequential reaction of ethylene diamine with propylene oxide and ethylene oxide in the presence of a catalyst, said surfactant containing polyoxypropylene chains having an average molecular weight of between about 750 and about 6,750 and polyoxyethylene chains constituting between about 10 and about 80 weight percent of said surfactant.

5. A reagent formulation as set forth in claim 4 wherein the nitrogen-containing surfactant is solid and the polyoxypropylene chains thereof have an average molecular weight of less than about 4,000.

6. A reagent formulation as set forth in claim 5 wherein the polyoxypropylene chains of the surfactant have an average molecular weight of about 2,750 and the weight percentage of the polyoxyethylene units is about 70%.

7. A reagent formulation for use in assaying a biological specimen for glutamic pyruvic transaminase comprising a granular, water-soluble, substantially anhydrous, storage-stable mixture containing reduced nicotinamide adenine dinucleotide disodium salt, gum arabic, tris-(hydroxymethyl)-aminomethane, a carbohydrate polymer, bovine serum albumin, lactate, dehydrogenase, ammonium sulfate, DL-alanine, dibasic sodium phosphate, monobasic sodium phosphate, and a nitrogen-containing polyoxyalkylene nonionic surfactant obtained by the sequential reaction of ethylenediamine with propylene oxide and ethylene oxide in the presence of a catalyst, said surfactant containing polyoxypropylene chains having an average molecular weight of between about 750 and about 6,750 and polyoxyethylene chains constituting between about 10 and about 80 weight percent of said surfactant.

8. A reagent formulation as set forth in claim 7 wherein the nitrogen-containing surfactant is solid and the polyoxypropylene chains thereof have an average molecular weight of less than about 4,000.

9. A reagent formulation as set forth in claim 8 wherein the polyoxypropylene chains of the surfactant have an average molecular weight of about 2,750 and the weight percentage of the polyoxyethylene units is about 70%.

10. A method of preparing a granular, water-soluble, substantially anhydrous, storage-stable reagent formulation for use in assaying a biological specimen for glutamic oxaloacetic transaminase which comprises preparing a mixture containing L-aspartic acid, malate dehydrogenase, reduced nicotinamide adenine dinucleotide disodium salt, bovine serum albumin, a carbohydrate polymer, tris-(hydroxymethyl)-aminomethane, succinic acid, gum arabic, a solid nitrogen-containing polyoxyalkylene nonionic surfactant obtained by the sequential reaction of ethylenediamine with propylene oxide and ethylene oxide in the presence of a catalyst, said surfactant containing polyoxypropylene chains having an average molecular weight of between about 750 and about 6,750, and polyoxyethylene chains constituting between about 10 and about 80 weight percent of said surfactant, and a solvent for the surfactant; and removing the solvent to form a substantially anhydrous, free-flowing water-soluble, granular solid.

11. A method as set forth in claim 10 wherein the nitrogen-containing surfactant is solid and the polyoxypropylene chains thereof have an average molecular weight of less than about 4,000.

12. A method as set forth in claim 11 wherein the polyoxypropylene chains of the surfactant have an average molecular weight of about 2,750 and the weight percentage of the polyoxyethylene units thereof is about 70%.

13. A method of preparing a granular, water-soluble, substantially anhydrous, storage-stable reagent formulation for use in assaying a biological specimen for glutamic pyruvic transaminase which comprises preparing a mixture containing reduced nicotinamide adenine dinucleotide disodium salt, gum arabic, tris-(hydroxymethyl)-aminomethane, a carbohydrate polymer, bovine serum albumin, lactate dehydrogenase, ammonium sulfate, DL-alanine, dibasic sodium phosphate, monobasic sodium phosphate, a nitrogen-containing polyoxyalkylene nonionic surfactant obtained by the sequential reaction of ethylene diamime with propylene oxide and ethylene oxide in the presence of a catalyst, said surfactant containing polyoxypropylene chains having an average molecular weight of between about 750 and 6,750, and polyoxyethylene chains constituting between about 10 and about 80 weight percent of the surfactant, and a solvent for the surfactant; and removing the solvent to form a substantially anhydrous, free-flowing, water-soluble, granular solid.

14. A method as set forth in claim 13 wherein the nitrogen-containing surfactant is solid and the polyoxypropylene chains thereof have an average molecular weight of less than about 4,000.

15. A method as set forth in claim 14 wherein the polyoxypropylene chains of the surfactant have an average molecular weight of about 2,750 and the weight percentage of the polyoxyethylene units thereof is about 70%.

16. A method of preparing a granular water-soluble, free-flowing, substantially anhydrous, storage-stable reagent formulation for use in assaying a biological specimen for a transaminase which comprises preparing a mixture containing sodium alpha-ketoglutarate, mannitol, a nitrogen-containing polyoxyalkylene nonionic surfactant obtained by the sequential reaction of ethylenediamine with propylene oxide and ethylene oxide in the presence of a catalyst, said surfactant containing polyoxypropylene chains having an average molecular weight of between about 750 and 6,750, and polyoxyethylene chains constituting between about 10 and about 80 weight percent of the surfactant, and a solvent for the surfactant; and removing the solvent to form a substantially anhydrous, free-flowing, water-soluble, granular solid.

17. A method as set forth in claim 16 wherein the nitrogen-containing surfactant is solid and the polyoxypropylene chains thereof have an average molecular weight of less than about 4,000.

18. A method as set forth in claim 17 wherein the polyoxypropylene chains of the surfactant have an average molecular weight of about 2,750 and the weight percentage of the polyoxyethylene units thereof is about 70%.

19. A method of assaying a biological specimen for glutamic oxaloacetic transaminase using a plurality of solid, water-soluble, substantially anhydrous storage-stable reagent formulations respectively comprising:
1. a coenzyme reagent formulation containing:
   a. L-aspartic acid;
   b. malate dehydrogenase;
   c. reduced nicotinamide adenine dinucleotide disodium salt;
   d. bovine serum albumin;
   e. a carbohydrate polymer;
   f. tris-(hydroxymethyl)-aminomethane;
   g. succinic acid;
   h. gum arabic; and
   i. a nitrogen-containing polyoxyalkylene nonionic surfactant obtained by the sequential reaction of ethylenediamine with propylene oxide and ethylene oxide in the presence of a catalyst, said surfactant containing polyoxypropylene chains having an average molecular weight of between about 750 and about 6,750 and polyoxyethylene chains constituting between about 10 and about 80 weight percent of said surfactant;
2. a substrate reagent formulation containing:
   a. sodium alpha-ketoglutarate;
   b. mannitol; and
   c. said nitrogen-containing polyoxyalkylene nonionic surfactant;
the method comprising the steps of:
   i. dissolving said reagents in separate portions of water to produce liquid reagents;
   ii. mixing the liquid reagent containing said coenzyme reagent formulation with a biological specimen to form a specimen/reagent test system;
   iii. incubating said system;
   iv. thereafter adding the liquid reagent containing said substrate reagent formulation to said system; and
   v. measuring a property of said system at two different predetermined points in time following the addition of said liquid reagent containing said substrate reagent formulation.

20. The method as set forth in claim 19 wherein said property of the system measured is light absorbance.

21. The method as set forth in claim 19 wherein said nitrogen-containing surfactant is solid and the polyoxypropylene chains thereof have an average molecular weight of less than about 4,000.

22. The method of assaying a biological specimen for glutamic pyruvic transaminase using a plurality of solid, water-soluble, substantially anhydrous, storage-stable reagent formulations respectively comprising:
1. a coenzyme reagent formulation containing:
   a. reduced nicotinamide adenine dinucleotide disodium salt;
   b. gum arabic;
   c. bovine serum albumin;
   d. a carbohydrate polymer;
   e. tris-(hydroxymethyl)-aminomethane;
   f. lactate dehydrogenase;
   g. ammonium sulfate;
   h. DL-alanine;
   i. dibasic sodium phosphate;
   j. monobasic sodium phosphate; and
   k. a nitrogen-containing polyoxyalkylene nonionic surfactant obtained by the sequential reaction of ethylenediamine with propylene oxide and ethylene oxide in presence of a catalyst, said surfactant containing polyoxypropylene chains having an average molecular weight of between about 750 and about 6,750; and
2. a substrate reagent formulation containing:
   a. sodium alpha-ketoglutarate;
   b. mannitol; and
   c. said nitrogen-containing polyoxyalkylene nonionic surfactant;
the method comprising the steps of:
   i. dissolving said reagents in separate portions of water to produce liquid reagents;

ii. mixing the liquid reagent containing said coenzyme reagent formulation with a biological specimen to form a specimen/reagent test system;
iii. incubating said system;
iv. thereafter adding the liquid reagent containing said substrate reagent formulation to said system; and
v. measuring a property of said system at two different predetermined points in time following the addition of said liquid reagent containing said substrate reagent formulation.

23. The method as set forth in claim 22 wherein said property of the system measured is light absorbance.

24. The method as set forth in claim 22 wherein said nitrogen-containing surfactant is solid and the polyoxypropylene chains thereof have an average molecular weight of less than about 4,000.

* * * * *